United States Patent [19]

Mody et al.

[11] Patent Number: 4,788,220

[45] Date of Patent: Nov. 29, 1988

[54] PEDIATRIC IBUPROFEN COMPOSITIONS

[75] Inventors: Dhiraj S. Mody, Hammonton; Annabelle Mogavero, Deptford, both of N.J.

[73] Assignee: American Home Products Corporation (Del.), New York, N.Y.

[21] Appl. No.: 71,115

[22] Filed: Jul. 8, 1987

[51] Int. Cl.$^4$ .............................................. A61K 31/19
[52] U.S. Cl. .................................................... 514/557
[58] Field of Search ............... 424/488, 485, 484, 486, 424/456; 514/557

[56] References Cited

U.S. PATENT DOCUMENTS

| 4,145,440 | 3/1979 | Fitch | 424/287 |
|---|---|---|---|
| 4,346,108 | 8/1982 | Singer | 424/317 |
| 4,361,580 | 11/1982 | Peck et al. | 424/287 |
| 4,569,937 | 2/1986 | Baker et al. | 514/557 X |
| 4,571,400 | 2/1986 | Arnold | 514/557 X |
| 4,681,897 | 7/1987 | Brand | 514/557 |
| 4,684,666 | 8/1987 | Haas | 514/557 |
| 4,689,218 | 8/1987 | Gazzaniga et al. | 514/557 X |
| 4,690,823 | 9/1987 | Lohner et al. | 424/456 |
| 4,695,591 | 9/1987 | Hanna et al. | 424/488 X |
| 4,713,249 | 12/1987 | Schroeder | 424/488 |

*Primary Examiner*—Nancy A. B. Swisher
*Attorney, Agent, or Firm*—John W. Routh

[57] ABSTRACT

A pediatric ibuprofen composition is provided wherein the ibuprofen remains in suspension and wherein the bitter taste of ibuprofen is masked, the primary suspending agents being xanthan gum, microcrystalline cellulose, sodium carboxymelthylcellulose and polysorbate, and the primary taste masking agents being sucrose and sorbitol solution.

2 Claims, No Drawings

PEDIATRIC IBUPROFEN COMPOSITIONS

This invention relates to a pediatric ibuprofen composition wherein the ibuprofen remains in suspension and wherein the bitter taste of ibuprofen is masked. More particularly the invention relates to a pediatric ibuprofen composition wherein the ibuprofen is maintained in suspension by the primary suspending agents xanthan gum, microcrystalline cellulose, sodium carboxymethyl cellulose and polysorbate 80, and wherein the ibuprofen is taste-masked with sucrose and sorbitol solution.

BACKGROUND OF THE INVENTION

Pediatric ibuprofen compositions are known in the art and marketed commercially. One such suspension is described in U.S. Pat. No. 4,145,440 and teaches taste-masking the ibuprofen by first forming an aluminum salt of ibuprofen and then suspending the aluminum salt of ibuprofen in a pharmaceutical vehicle containing microcrystalline cellulose, sodium carboxymethylcellulose or magnesium aluminum silicate as preferred suspending agents, and water soluble surface active agents in a sorbitol/glycerin/water mixture. Similarly, U.S. Pat. No. 4,361,580 teaches taste-masking with an aluminum salt of ibuprofen in a vehicle containing a suspending agent with a particle size below 50 microns, a water-soluble surfactant, water and sucrose or its sweetening equivalent of glucose, fructose, sodium saccharin or sodium cyclamate. The suspending agents include acacia, tragacanth, xanthan gum, microcrystalline cellulose, and sodium carboxymethylcellulose and the surfactants include (z)-sorbitan-mono-9-octadecenoate and polysorbate 80.

Fluid suspensions of ibuprofen are also disclosed in U.S. Pat. No. 4,346,108 which describes various ibuprofen dosage forms. The example of liquid dosage form again contains the ibuprofen aluminum salt, citric acid, benzoic acid, sucrose, tragacanth, lemon oil and water. Acacia and methylcellulose are disclosed as other suspending agents.

DESCRIPTION OF THE INVENTION

It has now been found that a taste neutral pediatric composition can be formulated from micronized ibuprofen instead of aluminum salt of ibuprofen and that the ibuprofen can be maintained indefinitely in suspension by a combination of suspending agents including xanthan gum, microcrystalline cellulose, sodium carboxymethyl cellulose and polysorbate 80.

DETAILED DESCRIPTION OF THE INVENTION

The pediatric ibuprofen compositions of the invention contain about 1% to about 2% ibuprofen by weight of the total composition, about 0.1% to about 1.5% by weight of the total composition of suspension stabilizing agents consisting essentially of xanthan gum, microcrystalline cellulose, sodium carboxymethyl cellulose and polysorbate 80, about 55% to about 75% by weight of the total composition of a combination of taste masking agents consisting essentially of sucrose and sorbitol solution, the composition also containing citric acid as a flavor enhancer in an amount sufficient to adjust the pH to about 3.5 to 5 and water.

The pediatric ibuprofen composition is formulated to contain about 60 mg to about 120 mg of ibuprofen per teaspoon (5 ml) of formulation, preferably about 100 mg/5 ml.

Xanthan gum is an article of commerce and is marketed by R. T. Vanderbilt Company, Inc. of Los Angeles, Calif. under the tradename Rhodigel 23. It is a food grade thickener in powder form of about 80 mesh.

Ibuprofen is available commercially from Ethyl Corporation, Baton Rouge, La. in a particle size range of 100–250 microns.

Microcrystalline cellulose and sodium carboxymethylcellulose are available from FMC Corporation, Newark, Del., the former under the brand name Avicel CL 611.

Coloring and flavoring agents can be added as desired. The other ingredients can be any national formulary or USP grades. The invention is further described by reference to the following examples.

EXAMPLE 1

A pediatric ibuprofen formulation was prepared having the following compositions:

| Ingredient | Percent Wt/vol. | Grams per 15 liters |
|---|---|---|
| Xanthan Gum | 0.10 | 15.0 |
| Microcrystalline Cellulose | 0.75 | 112.5 |
| Sodium Benzoate, NF | 0.25 | 37.5 |
| Citric Acid, Hydrous, USP | 0.25 | 37.5 |
| Sucrose, NF | 50.00 | 7500.0 |
| Glycerin, USP | 10.00 | 1500.0 |
| Sorbitol Solution, USP | 10.00 | 1500.0 |
| Ibuprofen USP | 1.60 | 240.0 |
| Sodium Carboxymethylceliulose, USP | 0.10 | 15.0 |
| Polysorbate 80, NF | 0.10 | 15.0 |
| Red FDC 40 | 0.015 | 2.25 |
| Disodium Edetate, USP | 0.05 | 7.5 |
| Artificial flavor | 0.88 | 132.0 |
| Purified Water Deionized, USP | qs. to 100 ml | qs to 15000 ml. |

The procedure for preparation of the above pediatric formulation is first to prepare an ibuprofen slurry. The sorbitol solution and glycerin were weighed into a jacketed kettle equipped with a stirrer. The sodium carboxymethyl cellulose was sprinkled onto the solution and mixed for 10 minutes until all of the particles were completely wet. The mixture was then heated to about 70° C. and mixed until the gum was completely hydrated. The mixture was then cooled to 45° C. and the polysorbate 80 was added. Mixing was continued while cooling the mixture to 30° C. The ibuprofen was then sprinkled slowly into the mixture and mixing was continued for 15 minutes.

The xanthan gum solution was prepared first in the form of a 1% by weight solution in water. The required amount of water was placed into a mixing bowl equipped with a Lightnin mixer and the xanthan gum slowly added and hydrated by mixing at high shear for approximately 25 minutes. Into a separate mixing vessel, equipped with a Lightnin mixer was placed 30% of the water required for the batch (about 4500 ml.) The microcrystalline cellulose was sprinkled onto the water and mixing at medium shear for 30 minutes was continued in order to completely suspended the microcrystalline cellulose. The required amount of the xanthan gum solution was added to the microcrystalline cellulose suspension with mixing for 15 minutes or until a uniform suspension was obtained.

The sucrose was then added slowly with mixing for 15 minutes, or until no sucrose particles are observed, and the coloring was added. The required amount of the ibuprofen slurry was slowly added from the first step and mixed for 15 minutes. The sodium benzoate, disodium edetate and citric acid were sequentially added and mixed for 5 minutes. The citric acid and the flavoring agents were sequentially added with mixing for 5 minutes after each addition. The remainder of the water then added with mixing until the formulation was homogeneous.

The initial viscosity of the final formulation at 24° C. was 1250 cps with a #2 spindle at 4 RPM and at 10 RPM the viscosity was 600 cps. On standing the viscosity increased to 4000 cps which on shaking for 5 seconds decreased to 1200 cps. The initial pH of the formulation was 4.10 and the specific gravity was 1.24 gram/milliter.

EXAMPLE 2

A pediatric ibuprofen formulation was prepared having the following composition:

| Ingredient | Percent Wt/vol. | Grams per 15 liters |
| --- | --- | --- |
| Xanthan Gum | 0.10 | 15.0 |
| Microcrystalline Cellulose | 0.75 | 112.5 |
| Sodium Benzoate, NF | 0.25 | 37.5 |
| Citric Acid, Hydrous, USP | 0.25 | 37.5 |
| Sucrose, NF | 50.00 | 7500.0 |
| Glycerin, USP | 10.00 | 1500.0 |
| Sorbitol Solution, USP | 10.00 | 1500.0 |
| Ibuprofen, USP | 1.60 | 240.0 |
| Sodium Carboxymethylcellulose, USP | 0.10 | 15.0 |
| Polysorbate 80, NF | 0.30 | 45.0 |
| Red FDC 40 | 0.015 | 2.25 |
| Disodium Edetate, USP | 0.05 | 7.5 |
| Artificial flavor | 0.88 | 132.0 |
| Purified Water, Deionized, USP | qs. to 100 ml | qs to 15000 ml. |

The procedure for preparation of the above pediatric formulation is first to prepare an ibuprofen slurry. The sorbitol solution was weighed into a jacketed kettle equipped with a stirrer. The sodium carboxymethyl cellulose was sprinkled onto the solution and mixed for 10 minutes until all of the particles were completely wet. The glycerin was added with mixing for 5 minutes and the mixture was then heated to about 70° C. the temperature held for at least 30 minutes to make sure the gum is completely hydrated and then the temperature was reduced to 45° C. The polysorbate 80 was added. Mixing was continued while cooling the mixture to 30° C. The ibuprofen was then sprinkled slowly into the mixture and mixing was continued for 15 minutes.

The xanthan gum solution was prepared first in the form of a 1% by weight solution in water. The required amount of water, 1980 grams, was placed into a mixing bowl equipped with a Lightnin mixer and 20 grams of the xanthan gum slowly added and hydrated by mixing at high shear for approximately 25 minutes. Into a separate mixing vessel, equipped with a Lightnin mixer having a large propeller was placed 30% of the water required for the batch. The microcrystalline cellulose was sprinkled onto the water and mixing at medium shear for 30 minutes was continued in order to completely suspend the microcrystalline cellulose. The required amount of the xanthan gum solution was added to the microcrystalline cellulose solution with mixing for 15 minutes of until a uniform solution was obtained.

The sucrose was then added slowly with mixing for 15 minutes, or until no sucrose particles are observed, and the coloring was added. The sodium benzoate and disodium edetate were sequentially added and mixed for 5 minutes. The citric acid and the flavoring agents were sequentially added with mixing for 5 minutes after each addition. The required amount of the ibuprofen slurry was slowly added from the first step and mixed for 15 minutes. The remainder of the water then added with mixing until the formulation was homogeneous.

The viscosity of the final formulation at 24° C. was 1100 cps with a #2 spindle at 4 RPM and at 10 RPM the viscosity was 950 cps. The initial pH of the formulation was 4.10 and the specific gravity was 1.234 gram/milliliter. On standing the viscosity increased to 3800 cps which in shaking for 5 seconds decreased to 1200 cps.

The procedure for preparation of the above pediatric formulation was essentially the same as that of Example 2.

The viscosity of the final formulation at 24° C. was 1000 cps with a #2 spindle at 4 RPM. The initial pH of the formulation was 4.22 and the specific gravity was 1.24 gram/milliliter. On standing the viscosity increased to 4200 cps which on shaking for 5 seconds decreased to 1200 cps. The product was a cherry red opaque liquid with a sweet tutti-frutti taste.

EXAMPLE 3

A pediatric ibuprofen formulation was prepared having the following composition:

| Ingredient | Percent Wt/vol. | Grams per 2 liters |
| --- | --- | --- |
| Xanthan Gum | 0.10 | 0.20 |
| Microcrystalline Cellulose | 0.75 | 1.50 |
| Sodium Benzoate, NF | 0.25 | 0.50 |
| Citric Acid, Hydrous, USP | 0.25 | 0.50 |
| Sucrose, NF | 50.00 | 100.00 |
| Glycerin, USP | 10.00 | 20.00 |
| Sorbitol Solution, USP | 10.00 | 20.00 |
| Ibuprofen, USP | 200 | 4.00 |
| Sodium Carboxymethylcellulose, USP | 0.10 | 0.20 |
| Polysorbate 80, NF | 0.30 | 0.60 |
| Red FDC 40 | 0.015 | 0.03 |
| Disodium Edetate, USP | 0.05 | 0.10 |
| Artificial flavor | 0.88 | 1.76 |
| Purified Water, Deionized, USP | qs. to 100 ml | qs to 100 ml. |

We claim:

1. A taste neutral pediatric ibuprofen composition containing about 1% to about 2% weight ibuprofen by volume of the total composition comprising a primary suspension stabilizing combination of ingredients and a primary taste masking combination of ingredients, the suspension stabilizing combination of ingredients comprising about 1.25% to about 1.5% weight suspension stabilizing combination by volume of the total composition and consisting essentially of xanthan gum, microcrystalline cellulose, sodium carboxymethylcellulose and polysorbate 80, the taste masking combination comprising about 55% to about 75% weight taste masking combination by volume of the total composition and consisting essentially of sucrose and sorbitol solution, the composition also containing citric acid as a flavor enhancer in an amount sufficient to adjust the pH to about 3.5 and 5 and water qs to 100% by volume of the composition.

2. The pediatric ibuprofen composition of claim 1 also containing flavoring agents and having an ibuprofen concentration of about 50 mg to about 100 mg per 5 ml of composition.

* * * * *